United States Patent
Tesar et al.

(10) Patent No.: US 10,918,610 B2
(45) Date of Patent: Feb. 16, 2021

(54) COMPOUNDS AND METHODS OF PROMOTING MYELINATION

(71) Applicant: Case Western Reserve University, Cleveland, OH (US)

(72) Inventors: Paul Tesar, Wickliffe, OH (US); Drew Adams, Cleveland, OH (US); Steven B. Landau, Wellesley, MA (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/229,875

(22) Filed: Dec. 21, 2018

(65) Prior Publication Data
US 2019/0314300 A1    Oct. 17, 2019

Related U.S. Application Data

(60) Provisional application No. 62/609,744, filed on Dec. 22, 2017.

(51) Int. Cl.
*A61K 31/135* (2006.01)
*A61P 25/28* (2006.01)

(52) U.S. Cl.
CPC ............ *A61K 31/135* (2013.01); *A61P 25/28* (2018.01)

(58) Field of Classification Search
CPC .............................. A61K 31/135; A61P 25/28
USPC ........................................................ 514/646
See application file for complete search history.

(56) References Cited

U.S. PATENT DOCUMENTS

| | | | |
|---|---|---|---|
| 5,354,781 A | * | 10/1994 | Breliere ............... C07C 211/35 514/650 |
| 6,482,986 B1 | | 11/2002 | Boigegrain et al. |
| 2007/0123556 A1 | | 5/2007 | Pennypacker et al. |
| 2008/0089861 A1 | | 4/2008 | Went et al. |
| 2010/0092479 A1 | | 4/2010 | Johansen et al. |
| 2015/0232444 A1 | | 8/2015 | De Brabander et al. |
| 2018/0228743 A1 | | 8/2018 | Tesar et al. |
| 2019/0269670 A1 | | 9/2019 | Tesar et al. |

FOREIGN PATENT DOCUMENTS

| | | |
|---|---|---|
| WO | 2010/021681 A2 | 2/2010 |
| WO | 2015/088625 A2 | 6/2015 |
| WO | 2018/022904 A2 | 2/2018 |

OTHER PUBLICATIONS

Copending U.S. Appl. No. 15/880,184, filed Jan. 25, 2018 (Year: 2018).*
Harlow et al, Frontiers in Neurology (2015), vol. 6, pp. 1-13. (Year: 2015).*
Bourrie et al., SSR125329A, a high affinity sigma receptor ligand with potent anti-inflammatory properties. Eur J Pharmacol. Dec. 5, 2002;456(1-3):123-31.

(Continued)

*Primary Examiner* — Craig D Ricci
*Assistant Examiner* — Janet L. Coppins
(74) *Attorney, Agent, or Firm* — McCarter & English, LLP; Steven G. Davis; Wei Song

(57) ABSTRACT

The invention is a method of treating a subject with primary progressive or secondary progressive multiple sclerosis. The method comprises administering an effect amount of Cis-N-cyclohexyl-N-ethyl-3-(3-chloro-4-cyclohexylphenyl) prop-2-enylamine or a pharmaceutically acceptable salt thereof to the subject.

2 Claims, 6 Drawing Sheets

Oligodendrocyte formation

(56) References Cited

OTHER PUBLICATIONS

Casellas et al., Immunopharmacological profile of SR 31747: in vitro and in vivo studies on humoral and cellular responses. J Neuroimmunol. Jul. 1994:52(2)193-203.

Chao et al., Preliminary Evidence of Increased Hippocampal Myelin Content in Veterans with Posttraumatic Stress Disorder. Front Behav Neurosci. Dec. 2, 2015;9:333. 8 pages.

Ekins et al., Three-dimensional quantitative structure-activity relationship analysis of human CYP51 inhibitors. Drug Metab Dispos. Mar. 2007;35(3):493-500.

Genetics Home Reference, Metachromatic leukodystrophy. Retrieved online at: https://ghr.nlm.nih.gov/condition/metachromatic-leukodystrophy, 6 pages, Feb. 2013.

Reitz, Toward precision medicine in Alzheimer's disease. Ann Transl. Med. Mar. 2016;4(6):107. 7 pages.

Stanford Health Now, Alzheimer's Prevention, Treatment and Research—A Q&A with Dr. Frank Longo. Retrieved online at: https://stanfordhealthcare.org/stanford-health-now/2016/alzheimers-prevention-treatment-research-qa-longo.html, 2 pages, Jan. 29, 2016.

Stankiewicz et al., Role of Immunosuppressive Therapy for the Treatment of multiple Sclerosis, Neurotherapeutics, vol. 10, No. 1, Dec. 28, 2012, pp. 77-88.

Bourrie et al., Enhancement of endotoxin-induced interleukin-10 production by SR 31747A, a sigma ligand, Eur. J. Immunol. 1995. 25:2882-2287.

Bradl et al., Oligodendrocytes: biology and pathology. Acta Neuropathol. Jan. 2010;119(1):37-53.

Chao et al., Increased Hippocampal Myelin Content in Veterans with Posttraumatic Stress Disorder. Front Behav Neurosci. Dec. 2, 2015;9:333. 8 pages.

Google.com, relieve. 1 page, accessed Oct. 9, 2018.

Labit-Le Bouteiller et al., Antiproliferative effects of SR31747A in animal cell lines are mediated by inhibition of cholesterol biosynthesis at the sterol isomerase step. Eur J Biochem. Sep. 1, 1998;256(2):342-9.

Paul et al., Allosteric modulation of peripheral sigma binding sites by a new selective ligand: SR 31747. J Neuroimmunol. Jul. 1994;52(2):183-92.

U.S. Appl. No. 15/880,184, filed Jan. 25, 2018.
U.S. Appl. No. 16/320,554, filed Jan. 25, 2019.

\* cited by examiner

Oligodendrocyte formation

EBP inhibition

COMPOUNDS AND METHODS OF PROMOTING MYELINATION

CROSS REFERENCE TO RELATED APPLICATION

This application claims the benefit of priority from U.S. Provisional Application No. 62/609,744, filed Dec. 22, 2017, the disclosures of which are incorporated herein by reference in their entireties.

GOVERNMENT FUNDING

This invention was made with government support under Grant No. R01NS095280, awarded by the National Institute of Health. The United States government has certain rights to the invention.

BACKGROUND

Multiple sclerosis (MS) is a demyelinating disease in which the insulating covers of nerve cells in the brain and spinal cord are damaged. This damage disrupts the ability of parts of the nervous system to communicate, resulting in a range of signs and symptoms, including physical, mental, and sometimes psychiatric problems. Specific symptoms can include double vision, blindness in one eye, muscle weakness, trouble with sensation, or trouble with coordination.

The three main characteristics of multiple sclerosis are the formation of lesions in the central nervous system (also called plaques), inflammation, and the destruction of myelin sheaths of neurons. Multiple sclerosis also involves the loss of oligodendrocytes, the cells responsible for creating and maintaining a fatty layer-known as the myelin sheath-which helps the neurons carry electrical signals (action potentials). This results in a thinning or complete loss of myelin and, as the disease advances, the breakdown of the axons of neurons. When the myelin is lost, a neuron can no longer effectively conduct electrical signals. A repair process, called remyelination, takes place in early phases of the disease, but the oligodendrocytes are unable to completely rebuild the cell's myelin sheath. Repeated attacks lead to successively less effective remyelinations, until a scar-like plaque is built up around the damaged axons. These scars are the origin of the symptoms.

Several phenotypes (commonly termed types), or patterns of progression, have been described. Phenotypes use the past course of the disease in an attempt to predict the future course. They are important not only for prognosis but also for treatment decisions. Currently, the United States National Multiple Sclerosis Society and the Multiple Sclerosis International Federation, describes four types of MS (revised in 2013):

1. Clinically isolated syndrome (CIS)
2. Relapsing-remitting MS (RRMS)
3. Primary progressive MS (PPMS)
4. Secondary progressive MS (SPMS)

Relapsing-remitting multiple sclerosis is characterized by unpredictable relapses followed by periods of months to years of relative quiet (remission) with no new signs of disease activity. Deficits that occur during attacks may either resolve or leave problems, the latter in about 40% of attacks and being more common the longer a person has had the disease. This describes the initial course of 80% of individuals with multiple sclerosis. The relapsing-remitting subtype usually begins with a clinically isolated syndrome (CIS). In CIS, a person has an attack suggestive of demyelination, but does not fulfill the criteria for multiple sclerosis. 30 to 70% of persons experiencing CIS later develop multiple sclerosis.

Primary progressive multiple sclerosis occurs in approximately 10-20% of individuals, with no remission after the initial symptoms. It is characterized by progression of disability from onset, with no, or only occasional and minor, remissions and improvements. The usual age of onset for the primary progressive subtype is later than of the relapsing-remitting subtype. It is similar to the age that secondary progressive usually begins in relapsing-remitting multiple sclerosis, around 40 years of age.

Secondary progressive multiple sclerosis occurs in around 65% of those with initial relapsing-remitting multiple sclerosis, who eventually have progressive neurologic decline between acute attacks without any definite periods of remission. Occasional relapses and minor remissions may appear. The most common length of time between disease onset and conversion from relapsing-remitting to secondary progressive multiple sclerosisis 19 years.

Other, unusual types of multiple sclerosis have been described; these include Devic's disease, Balo concentric sclerosis, Schilder's diffuse sclerosis, and Marburg multiple sclerosis. There is debate on whether they are multiple sclerosisvariants or different diseases. Multiple sclerosis behaves differently in children, taking more time to reach the progressive stage. Nevertheless, they still reach it at a lower average age than adults usually do.

Currently there are a number of treatments available for multiple sclerosis. However, there treatments are generally effective mostly for the relapsing-remitting multiple sclerosis and none are able to promote remyelination. Because demyelination is prominent in primary progressive multiple sclerosis and secondary progressive multiple sclerosis, the available treatments for these types of multiple sclerosis are inadequate. There is the potential to develop effective treatments of these stages of multiple sclerosis by identifying compounds which promote the differentiation, maturation and proliferation of oligodendrocyte progenitors, which can stimulate and enhance the generation of new oligodendrocytes and intrinsic myelination and/or remyelination. Therefore, there is a need for compounds and therapeutic methods capable of enhancing the generation of new oligodendrocytes.

SUMMARY

It has now been found that the compound Cis-N-cyclohexyl-N-ethyl-3-(3-chloro-4-cyclohexylphenyl)prop-2-enylamine enhances the formation of oligodendrocytes (including specifically myelin regulatory factor-positive oligodendrocytes) from oligodendrocyte progenitor cells (OPCs) (see e.g., Examples 1, 4); and enhances the production of myelin sheaths by oligodendrocytes (see e.g., Example 2) in in vitro cell cultures and human brain-like miniature organ systems, both of which are desirable effects in demyelinating diseases where enhanced myelination or remyelination would be beneficial to the subject. Furthermore and significantly, it has also been found that the compound Cis-N-cyclohexyl-N-ethyl-3-(3-chloro-4-cyclohexylphenyl)prop-2-enylamine enhances or promotes remyelination of the nerve cells in the spinal cord (see e.g., Example 7) and in the brain (see e.g., Example 8) of laboratory animals, where the natural myelin sheaths protecting these nerve cells have been previously damaged, as they typically would be in demyelinating diseases such as multiple sclerosis, in particular primary progressive multiple sclerosis and secondary progressive multiple sclerosis. Based on these results, methods of treating primary progressive multiple sclerosis and secondary progressive multiple sclerosis are disclosed herein.

One embodiment of the invention is a method of treating a subject with primary progressive multiple sclerosis. The method comprises administering an effect amount of Cis-N-cyclohexyl-N-ethyl-3-(3-chloro-4-cyclohexylphenyl)prop-2-enylamine or a pharmaceutically acceptable salt thereof to the subject.

Another embodiment of the invention is a method of treating a subject with secondary progressive multiple sclerosis. The method comprises administering an effect amount of Cis-N-cyclohexyl-N-ethyl-3-(3-chloro-4-cyclohexylphenyl)prop-2-enylamine or a pharmaceutically acceptable salt thereof to the subject.

Another embodiment of the invention is Cis-N-cyclohexyl-N-ethyl-3-(3-chloro-4-cyclohexylphenyl)prop-2-enylamine or a pharmaceutically acceptable salt thereof for treating a subject with primary progressive multiple sclerosis.

Another embodiment of the invention is Cis-N-cyclohexyl-N-ethyl-3-(3-chloro-4-cyclohexylphenyl)prop-2-enylamine or a pharmaceutically acceptable salt thereof for treating a subject with secondary progressive multiple sclerosis.

Another embodiment of the invention is the use Cis-N-cyclohexyl-N-ethyl-3-(3-chloro-4-cyclohexylphenyl)prop-2-enylamine or a pharmaceutically acceptable salt thereof for the manufacture of a medicament for treating a subject with primary progressive multiple sclerosis.

Another embodiment of the invention is the use Cis-N-cyclohexyl-N-ethyl-3-(3-chloro-4-cyclohexylphenyl)prop-2-enylamine or a pharmaceutically acceptable salt thereof for the manufacture of a medicament for treating a subject with secondary progressive multiple sclerosis.

BRIEF DESCRIPTION OF THE DRAWINGS

FIGS. 7(A-F) illustrate the study evaluating the in vivo generation of newly myelinated fibers within the spinal cord following induced focal demyelination in the dorsal column of the spinal cord of C57BL/6 female mice.

FIGS. 8(A-B) illustrate the study evaluating the in vivo recovery of the fractional anisotropy (FA) value on the ipsilateral side following induced demyelination in the corpus callosum of Sprague-Dawley male rats.

DETAILED DESCRIPTION

Figure 1A:
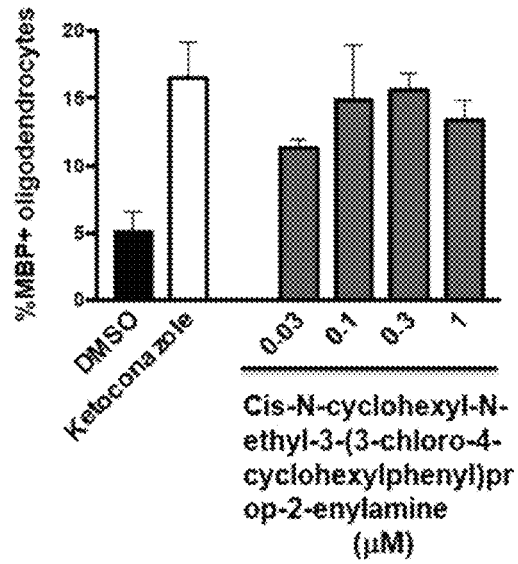
FIGS. 1(A-B) illustrate graphs showing the effect of the benzene derivative Cis-N-cyclohexyl-N-ethyl-3-(3-chloro-4-cyclohexylphenyl)prop-2-enylamine (concentrations=0.03 µM, 0.1 µM, 0.3 µM, 1 µM) on oligogdendrocyte formation (FIG. 1A) and EBP inhibition (FIG. 1B).

The invention is based on the discovery that the compound Cis-N-cyclohexyl-N-ethyl-3-(3-chloro-4-cyclohexylphenyl)prop-2-enylamine enhances the formation of oligodendrocytes (see Example 9). Oligodendrocytes can promote myelination and/or remyelination of nerves. Primary progressive multiple sclerosis and secondary progressive multiple sclersosis are characterized by extensive loss of myelin sheaths that surround nerve cells in the brain and spinal cord. Cis-N-cyclohexyl-N-ethyl-3-(3-chloro-4-cyclohexylphenyl)prop-2-enylamine is therefore ideally suited for treating these subtypes of multiple sclerosis.

The invention is a method of treating a subject with primary progressive multiple sclerosis by administrating an effective amount of Cis-N-cyclohexyl-N-ethyl-3-(3-chloro-4-cyclohexylphenyl)prop-2-enylamine to the subject. Primary progressive multiple sclerosis is identified by steadily worsening neurologic functions from the onset of symptoms without distinct relapses (attacks or exacerbations) or remission. The rate of progression may vary with occasional plateaus and temporary minor improvements, but declining neurologic progression is continuous.

The invention is also a method of treating a subject with secondary progressive multiple sclerosis by administrating an effective amount of Cis-N-cyclohexyl-N-ethyl-3-(3-chloro-4-cyclohexylphenyl)prop-2-enylamine to the subject. Secondary progressive multiple sclerosis is a form of MS that typically follows relapsing-remitting multiple sclerosis. It is characterized by steady accumulation of disability without relapses. In secondary progressive multiple sclerosis, there is steady buildup of disability and relapses are considered rare. When attack does occur, recovery is usually slow and, in many cases, incomplete. Existing symptoms can get worse and physical mobility becomes increasingly difficult.

Cis-N-cyclohexyl-N-ethyl-3-(3-chloro-4-cyclohexylphenyl)prop-2-enylamine or a pharmaceutically acceptable salt thereof can be prepared according to methods disclosed in U.S. Pat. No. 5,354,781, the entire teachings of which are incorporated herein by reference.

Pharmaceutically acceptable salts of Cis-N-cyclohexyl-N-ethyl-3-(3-chloro-4-cyclohexylphenyl)prop-2-enylamine can be used in the disclosed methods. "Pharmaceutically acceptable salt" of a Cis-N-cyclohexyl-N-ethyl-3-(3-chloro-4-cyclohexylphenyl)prop-2-enylamine means a salt that is pharmaceutically acceptable and that possesses the desired pharmacological activity of the parent compound. For example, the salt can be an acid addition salt, e.g., a hydrochloride salt, an acetic salt, a benzene sulfonic acid salt and the like. Generally, such salts can be prepared by reacting Cis-N-cyclohexyl-N-ethyl-3-(3-chloro-4-cyclohexylphenyl)prop-2-enylamine with a stoichiometric amount of the appropriate acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The phrase "pharmaceutically acceptable" means, within the scope of sound medical judgment, suitable for use in contact with the tissues of human beings and animals without excessive toxicity, irritation, allergic response, or other problem or complication, commensurate with a reasonable benefit/risk ratio.

The term "treating" includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. In one aspect, the subject is a mammal. A patient refers to a subject afflicted with a disease or disorder.

The phrase "effective amount" refers to an amount of a therapeutic agent that produces some desired effect at a reasonable benefit/risk ratio applicable to any medical treatment. In certain embodiments, the term refers to that amount necessary or sufficient to reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

An "effective amount" of Cis-N-cyclohexyl-N-ethyl-3-(3-chloro-4-cyclohexylphenyl)prop-2-enylamine and salts thereof used in the methods of the present invention varies depending upon the manner of administration, the age and body weight of the subject, and the condition of the subject to be treated, and ultimately will be decided by those skilled in the art. The term "effective amount" refers to an amount (dose) effective in treating a subject, having, for example, a neurodegenerative disease (e.g. multiple sclerosis).

The term "pharmaceutical composition" refers to a formulation containing the disclosed agents, in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The pharmaceutical compositions of the present invention can be administered to a subject by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route.

Formulation of Cis-N-cyclohexyl-N-ethyl-3-(3-chloro-4-cyclohexylphenyl)prop-2-enylamine and pharmaceutically acceptable salts thereof for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. Cis-N-cyclohexyl-N-ethyl-3-(3-chloro-4-cyclohexylphenyl)prop-2-enylamine and pharmaceutically acceptable salts thereof can be formulated into pharmaceutical compositions containing pharmaceutically acceptable non-toxic excipients and carriers. The excipients are all components present in the pharmaceutical formulation other than the active ingredient or ingredients. Suitable excipients and carriers useful in the present invention are composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

The phrase "pharmaceutically acceptable carrier" is, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, Cis-N-cyclohexyl-N-ethyl-3-(3-chloro-4-cyclohexylphenyl)prop-2-enylamine and pharmaceutically acceptable salts thereof can be administered in combination with cognitive enhancing (nootropic) agents. Exemplary agents include any drugs, supplements, or other substances that improve cognitive function, particularly executive functions, memory, creativity, or motivation, in healthy individuals. Non limiting examples include racetams (e.g., piracetam, oxiracetam, and aniracetam), nutraceuticals (e.g., bacopa monnieri, panax ginseng, ginko biloba, and GABA), stimulants (e.g., amphetamine pharmaceuticals, methylphenidate, eugeroics, xanthines, and nicotine), L-Theanine, Tolcapone, Levodopa, Atomoxetine, and Desipramine.

Another strategy for treating a subject suffering from primary or secondary progressive multiple sclerosis is to administer an effective amount of a Cis-N-cyclohexyl-N-ethyl-3-(3-chloro-4-cyclohexylphenyl)prop-2-enylamine of a pharmaceutically acceptable salt thereof along with an effective amount of additional oligodendrocyte differentiation and/or proliferation inducing agent(s) and/or anti-neurodegenerative disease agent. Examples of anti-neurodegenerative disease agents include L-dopa, cholinesterase inhibitors, anticholinergics, dopamine agonists, steroids, and immunomodulators including interferons, monoclonal antibodies, and glatiramer acetate.

Therefore, in a further aspect of the invention, Cis-N-cyclohexyl-N-ethyl-3-(3-chloro-4-cyclohexylphenyl)prop-2-enylamine of a pharmaceutically acceptable salt thereof can be administered as part of a combination therapy with adjunctive therapies for treating neurodegenerative and myelin related disorders.

The phrase "combination therapy" embraces the administration of Cis-N-cyclohexyl-N-ethyl-3-(3-chloro-4-cyclohexylphenyl)prop-2-enylamine of a pharmaceutically acceptable salt thereof and a therapeutic agent as part of a specific treatment regimen intended to provide a beneficial effect from the co-action of these therapeutic agents. When administered as a combination, Cis-N-cyclohexyl-N-ethyl-3-(3-chloro-4-cyclohexylphenyl)prop-2-enylamine of a pharmaceutically acceptable salt thereof and a therapeutic agent can be formulated as separate compositions. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (e.g., surgery).

In another aspect of the invention, the therapeutic agents administered in a combination therapy with Cis-N-cyclohexyl-N-ethyl-3-(3-chloro-4-cyclohexylphenyl)prop-2-enylamine of a pharmaceutically acceptable salt thereof can include at least one anti-neurodegenerative agent such as but not limited to, an immunotherapeutic agent.

An immunotherapeutic agent for use in the methods of the present invention can include therapies which target the immune component of the disease and/or the acute inflammatory response evidenced during an acute attack in remitting-relapsing multiple sclerosis. Examples include, but are not limited to immunomodulators such as interferon beta-1a and beta-1b (Avonex and Betaseron respectively), natalizumab (Copaxone) natalizumab (Tysabri), glatiramer acetate (Copaxone) or mitoxantrone.

The invention is further illustrated by the following examples, which are not intended to limit the scope of the claims.

EXEMPLIFICATIONS

In the following Examples, the inventors show that regeneration of myelin is mediated by oligodendrocyte progenitor cells (OPCs), an abundant stem cell population in the CNS and the principal source of new myelinating oligodendrocytes. Loss of myelin-producing oligodendrocytes in the central nervous system (CNS) underlies a number of neurological diseases, including multiple sclerosis and diverse genetic diseases. Using high throughput chemical screening approaches, the inventors have identified CYP51, sterol 14-reductase, and EBP, a narrow range of enzymes within the cholesterol biosynthesis pathway, as drug targets to increase remyelination and oligodendrocyte formation. The inventors have found that chemical or genetic inhibition of these enzymes resulted in accumulation of Δ8,9-unsaturated sterol intermediates, which when independently supplied to OPCs enhanced formation of new oligodendrocytes. Functional studies showed that small molecule inhibitors of CYP51, sterol 14-reductase, and EBP induce accumulation of Δ8,9-unsaturated sterols in human brain tissue in vitro and mouse brain tissue in vivo. At the same doses, these molecules also enhance the rate of myelination in vivo in a lysolecithin-induced mouse model of focal demyelination. Collectively, the results provide a unifying mechanism-of-action for most known small-molecule enhancers of oligodendrocyte formation and highlight specific targets for the development of optimal remyelinating therapeutics.

Methods

No statistical methods were used to predetermine sample size.

Small Molecules

Cholesterol biosynthetic intermediates were purchased from Avanti Polar Lipids as a solid: Lanosterol, Zymosterol, Zymostenol, Lathosterol, Desmosterol, 7-dehydrodesmosterol and T-MAS. 14-dehydrozymostenol (cholesta-8,14-dien-(3-ol) was provided by Franz Bracher, Ludwig-Maximilians University of Munich Mouse OPC Preparation EpiSC-derived OPCs were obtained using in vitro differentiation protocols and culture conditions described previously. To ensure uniformity throughout all in vitro screening experiments, EpiSC-derived OPCs were sorted to purity by fluorescence activated cell sorting at passage five with conjugated CD 140a-APC (eBioscience, 17-1401; 1:80) and NG2-AF488 (Millipore, AB5320A4; 1:100) antibodies. Sorted batches of OPCs were expanded and frozen down in aliquots. OPCs were thawed into growth conditions for one passage before use in further assays. Cultures were regularly tested and shown to be *mycoplasma* free.

In Vitro Phenotypic Screening of OPCs

EpiSC-derived OPCs were grown and expanded in poly-ornithine (PO) and laminin-coated flasks with growth medium (DMEM/F12 supplemented with N2-MAX (R&D Systems), B-27 (ThermoFisher), GlutaMax (Gibco), FGF2 (10 µg/mL, R&D systems, 233-FB-025) and PDGF-AA (10 µg/mL, R&D systems, 233-AA-050) before harvesting for plating. The cells were seeded onto poly-D-lysine 96-well CellCarrier plates (PerkinElmer) coated with laminin (Sigma, L2020; 15 µg/ml) using multi-channel pipet. For the experiment, 800,000 cells/mL stock in differentiation medium (DMEM/F12 supplemented with N2-MAX and B-27) was prepared and stored on ice for 2 h. Then, 40,000 cells were seeded per well in differentiation medium and allowed to attach for 30 min before addition of drug. For dose-response testing of all molecules except sterols, a 1000× compound stock in dimethyl sulphoxide (DMSO) was added to assay plates with 0.1 µL solid pin multi-blot replicators (V & P Scientific; VP 409), resulting in a final primary screening concentration of 1×. Sterols were added to cells as an ethanol solution (0.2% final ethanol concentration). Positive control wells and DMSO vehicle controls were included in each assay plate. Cells were incubated under standard conditions (37° C., 5% $CO_2$) for 3 days and fixed with 4% paraformaldehyde (PFA) in phosphate buffered saline (PBS) for 20 min. Fixed plates were washed with PBS (200 µL per well) twice, permeabilized with 0.1% Triton X-100 and blocked with 10% donkey serum (v/v) in PBS for 40 min. Then, cells were labelled with MBP antibodies (Abcam, ab7349; 1:200) for 16 h at 4° C. followed by detection with Alexa Fluor conjugated secondary antibodies (1:500) for 45 min. Nuclei were visualized by DAPI staining (Sigma; 1 µg/ml). During washing steps, PBS was added using a multi-channel pipet and aspiration was performed using Biotek EL406 washer dispenser (Biotek) equipped with a 96-well aspiration manifold.

High-Content Imaging and Analysis

Plates were imaged on the Operetta High Content Imaging and Analysis system (PerkinElmer) and a set of 6 fields captured from each well resulting in an average of 1200 cells being scored per well. Analysis (PerkinElmer Harmony and Columbus software) began by identifying intact nuclei stained by DAPI; that is, those traced nuclei that were larger than 300 µm$^2$ in surface area. Each traced nucleus region was then expanded by 50% and cross-referenced with the mature myelin protein (MBP) stain to identify oligodendrocyte nuclei, and from this the percentage of oligodendrocytes was calculated. In some experiments, the total process length of MBP+ oligodendrocytes was calculated as previously described.

GC/MS-Based Sterol Profiling

EpiSC-derived OPCs were plated at one million cells per well in PDL- and laminin-coated six well plates with differentiation media. After 24 hours, cells were dissociated with Accutase, rinsed with saline, and cell pellets were frozen. For sterol analyses, cells were lysed in methanol (Sigma-Aldrich) with agitation for 30 minutes and cell debris removed by centrifugation at 10,000 rpm for 15 min. Cholesterol-d7 standard (25,26,26,26,27,27,27-$^2H_7$-cholesterol, Cambridge Isotope Laboratories) was added before drying under nitrogen stream and derivatization with 55 al of bis(trimethylsilyl)trifluoroacetamide/trimethylchlorosilane to form trimethylsilyl derivatives. Following derivatization at 60° C. for 20 minutes, 1 µl was analyzed by gas chromatography/mass spectrometry using an Agilent 5973 Network Mass Selective Detector equipped with a 6890 gas chromatograph system and a HP-5MS capillary column (60 µm×0.25 µm×0.25 mm). Samples were injected in splitless mode and analyzed using electron impact ionization. Ion fragment peaks were integrated to calculate sterol abundance, and quantitation was relative to cholesterol-d7. The following m/z ion fragments were used to quantitate each metabolite: cholesterol-d7 (465), FF-Mas (482), cholesterol (368), zymostenol (458), zymosterol (456), desmosterol (456, 343), 7-dehydrocholesterol (456, 325), lanosterol (393), lathosterol (458), 14-dehydrozymostenol (456). Calibration curves were generated by injecting varying concentrations of sterol standards and maintaining a fixed amount of cholesterol-D7. The human glioma cell line GBM528 was a gift of Jeremy Rich (Cleveland Clinic). Cortical organoids were generated as described previously.

Focal Demyelination, Drug Treatment and Histological Analysis

Focal demyelination in the dorsal column of the spinal cord was induced by the injection of 1% LPC solution. 12 week old C57BL/6 female mice were anesthetized using isoflurane and T10 laminectomies were performed. 1 µl of 1% LPC was infused into the dorsal column at a rate of 15 al/hour. At day 4, animals were randomized into treatment groups prior to treatment (2 animals were excluded due to surgical complications). Between days 4 and 11 post laminectomy, animals received daily injections of either vehicle or drug intraperitoneally. Drugs were dissolved in DMSO and ethanol or corn oil and then diluted with sterile saline for injections. This experiment was done in a blinded manner: compounds were coded to ensure the researchers performing the experiments were unaware of the treatment being administered to each animal. All animals were euthanized 12 days post laminectomy (n=4-6 per group). Mice were anesthetized using ketamine/xylazine rodent cocktail and then euthanized by transcardial perfusion with 4% PFA, 2% glutaraldehyde, and 0.1 M sodium cacodylate. Samples were osmicated, stained en bloc with uranyl acetate and embedded in EMbed 812, an Epon-812 substitute (EMS). 1 µm sections were cut and stained with toluidine blue and visualized on a light microscope (Leica DM5500B). The number of myelinated axons per unit areas was counted from sections in the middle of each lesion and then averaged over each treatment group. A Mann-Whitney statistical analysis was performed to assess statistical significance.

Analysis of Mouse Brain Sterol Levels

Ten to twelve week old male C57BL/6 mice were injected with Cis-N-cyclohexyl-N-ethyl-3-(3-chloro-4-cyclohexylphenyl)prop-2-enylamine dissolved in sterile saline daily for three days. Mice were anaesthetized with isoflurane and perfused with phosphate buffered saline to remove blood from the brain. Brains were collected and flash frozen using liquid nitrogen. The samples were pulverized and 50-100 milligrams of tissue were collected for further processing. A modified Folch protocol was used for extraction of sterols. Briefly, samples were resuspended in a 2:1 chloroform/methanol mixture and homogenized. Cell debris was removed by centrifugation at 4000 g for 10 min. The solution was dried under air and resuspended in hexane with a cholesterol-D7 standard and dried again. Lipids were derivatized with 70 al of bis(trimethylsilyl)trifluoroacetamide; 2 µls were injected and analyzed by GC/MS as described above.

Oligodendrocyte Formation and Imaging on Electrospun Microfibers

A 12-well plate containing Mimetex aligned scaffold (microfiber plate, AMSBIO, AMS.TECL-006-1X, Electrospun poly-L-lactide Scaffold, 2 µM fibre diameter cell crown inserts) was prepared as previously described. Briefly, inserts were sterilized with 70% ethanol and washed with PBS before being coated with polyornithine and laminin. After laminin coating, 100,000 cells/mL of EpiSC-derived OPCs were plated in differentiation medium. After 24 h the media was replaced with fresh media containing small molecule treatments. Every 48 h the media was replaced with fresh compound containing media for a total of 14 days. Plates were fixed with 4% PFA, permeabilized with 0.1% Triton X-100, and blocked with 10% donkey serum (v/v) in PBS for 60 min. Plates were stained for MBP (Abcam, ab7349; 1:100) and DAPI staining (Sigma; 5 µg/ml). After staining, the inserts were moved into new 12-well plate and covered with 2 mL of PBS before imaging in Operetta high content Imaging and analysis system. Plates were imaged on the Operetta High Content Imaging and Analysis system (PerkinElmer) and a set of 8 fields captured from each well resulting in an average of 45,000 cells being scored per well. Analysis (PerkinElmer Harmony and Columbus software) identified intact nuclei stained by DAPI and calculated the MBP signal intensity per cell per well. Microfiber insert tracking images were taken using a Leica DMi8 with a 20× Dry/NA 0.40 objective. Microfiber plate inserts were mounted using Flouromount-G (SouthernBiotech) and allowed to partially harden before coverslips were added and the insert ring was removed. Confocal images were obtained on a Leica SP8 confocal scanning microscope, with 40× oil/NA 1.30 objective. Confocal stacks of 0.336 µm z-steps were taken at 1024×1024. Each fluorophore was excited sequentially and all contrast and brightness changes were applied consistently between images.

Results

Example 1—Cis-N-cyclohexyl-N-ethyl-3-(3-chloro-4-cyclohexylphenyl)prop-2-enylamine Enhances Formation of DifferentiatedMBP+ Oligodendrocytes from OPCs In Vitro OPCs were generated from the EpiSC5 cell line. EpiSC-derived OPCs were obtained from the EpiSC5 cells using in vitro differentiation protocols and culture conditions described previously (Najm et al, 2012, Nature Methods). To ensure uniformity throughout all in vitro screening experiments, EpiSC-derived OPCs were sorted to purity by fluorescence activated cell sorting at passage five with conjugated CD 140a-APC (eBioscience, 17-1401; 1:80) and NG2-AF488 (Millipore, AB5320A4; 1:100) antibodies. EpiSC-derived OPCs were grown and expanded in poly-ornithine (PO) and laminin-coated flasks with growth medium (DMEM/F12 supplemented with N2-MAX (R&D Systems), B-27 (ThermoFisher), GlutaMax (Gibco), FGF2 (10 µg/mL, R&D systems, 233-FB-025) and PDGF-AA (10 µg/mL, R&D systems, 233-AA-050) before harvesting for plating. The cells were seeded onto poly-D-lysine 96-well CellCarrier plates (PerkinElmer) coated with laminin (Sigma, L2020; 15 µg/ml) using multi-channel pipet. For the experiment, 800,000 cells/mL stock in differentiation medium (DMEM/F12 supplemented with N2-MAX and B-27) was prepared and stored on ice for 2 h. Then, 40,000 cells were seeded per well in screening medium and allowed to attach for 30 min before addition of Cis-N-cyclohexyl-N-ethyl-3-(3-chloro-4-cyclohexylphenyl)prop-2-enylamine. Cis-N-cyclohexyl-N-ethyl-3-(3-chloro-4-cyclohexylphenyl)prop-2-enylamine was first dissolved in DMSO at a 1000× stock concentration prior to addition into cell culture. Final concentrations of 0.03 um, 0.1 um, 0.3 um and 1 um were used for testing. A 1000× compound stock in dimethyl sulphoxide (DMSO) was added to assay plates with 0.1 mL solid pin multi-blot replicators (V & P Scientific; VP 409), resulting in a final primary screening concentration of 1×. Positive controls (ketoconazole, 2.5 µM) and DMSO vehicle controls were included in each assay plate. Cells were incubated under standard conditions (37° C., 5% $CO_2$) for 3 days and fixed with 4% paraformaldehyde (PFA) in phosphate buffered saline (PBS) for 20 min. Fixed plates were washed with PBS (200 µL per well) twice, permeabilized with 0.1% Triton X-100 and blocked with 10% donkey serum (v/v) in PBS for 40 min. Then, cells were labelled with MBP antibodies (Abcam, ab7349; 1:200) for 1 h at room temperature (24° C. followed by detection with Alexa Fluor conjugated secondary antibodies (1:500) for 45 min. Nuclei were visualized by DAPI staining (Sigma; 1 μg/ml). During washing steps, PBS was added using a multi-channel pipet and aspiration was performed using Biotek EL406 washer dispenser (Biotek) equipped with a 96-well aspiration manifold.

Plates were imaged on the Operetta High Content Imaging and Analysis system (PerkinElmer) and a set of 6 fields captured from each well resulting in an average of 1200 cells being scored per well. Analysis (PerkinElmer Harmony and Columbus software) began by identifying intact nuclei stained by DAPI; that is, those traced nuclei that were larger than 300 μm$^2$ in surface area. Each traced nucleus region was then expanded by 50% and cross-referenced with the mature myelin protein (MBP) stain to identify oligodendrocyte nuclei, and from this the percentage of oligodendrocytes was calculated.

The results are shown in in FIG. 1A. As can be seen from the figure, Cis-N-cyclohexyl-N-ethyl-3-(3-chloro-4-cyclohexylphenyl)prop-2-enylamine enhances formation of MBP+ oligodendrocytes in culture.

Figure 4:
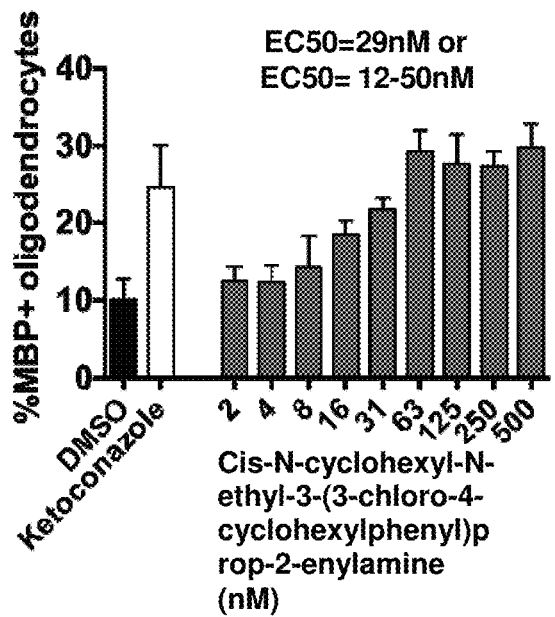
FIG. 4 is a bar graph illustrating the effect of Cis-N-cyclohexyl-N-ethyl-3-(3-chloro-4-cyclohexylphenyl)prop-2-enylamine (concentration range=2 nM to 500 nM) on differentiated MBP-positive oligogdendrocyte formation from OPCs in vitro, and a calculation of the $EC_{50}$ values based on the dose response data.

The experiments described above were repeated with a wider range of concentrations for the compound Cis-N-cyclohexyl-N-ethyl-3-(3-chloro-4-cyclohexylphenyl)prop-2-enylamine and with 50,000 cells instead of 40,000 cells that were being seeded per well in N2B27 media containing no growth factors. Consistent with FIG. 1A, FIG. 4 shows that Cis-N-cyclohexyl-N-ethyl-3-(3-chloro-4-cyclohexylphenyl)prop-2-enylamine enhances formation of MBP+ oligodendrocytes in in vitro cultures of OPCs. Significantly, t2w1he measured percentages of MBP+ oligodendrocytes shown in the bar graph FIG. 1A indicate that, at concentrations of 63 nM, 125 nM, 250 nM and 500 nM, which about 5-40 times lower than the concentration of 2.5 μM used for ketoconazole, Cis-N-cyclohexyl-N-ethyl-3-(3-chloro-4-cyclohexylphenyl)prop-2-enylamine increases the number of differentiated MBP+ dendrocytes from OPCs at higher rates than ketoconazole. Additionally, the EC$_{50}$ values were calculated to be about 29 nM or about 12-50 nM, using Collaborative Drug Discovery, and using The Levenberg-Marquardt algorithm to fit a Hill equation to dose-response data (0.5 nM to 1000 nM).

Example 2—Cis-N-cyclohexyl-N-ethyl-3-(3-chloro-4-cyclohexylphenyl)prop-2-enylamine Inhibits Formation of Cholesterol by Inhibiting EBP and Causes Accumulation of EBP Substrate Zymostenol in Cultures EpiSC Derived OPCs (In Vitro)

EpiSC-derived OPCs were plated at one million cells per well in PDL- and laminin-coated six well plates with differentiation media (DMEM/F12 supplemented with N2-MAX (R&D Systems), B-27 (ThermoFisher), GlutaMax (Gibco). In treated conditions, 100 nm of Cis-N-cyclohexyl-N-ethyl-3-(3-chloro-4-cyclohexylphenyl)prop-2-enylamine was added, while DMSO control was added to control media. After 24 hours, cells were dissociated with Accutase, rinsed with saline, and cell pellets were frozen. Cells were lysed in methanol (Sigma-Aldrich) with agitation for 30 minutes and cell debris removed by centrifugation at 10,000 rpm for 15 min. Cholesterol-d7 standard (Cambridge Isotope Laboratories) was added before drying under nitrogen stream and derivatization with 55 al of bis(trimethylsilyl) trifluoroacetamide. After derivatization, 1 al was analyzed by gas chromatography/mass spectrometry using an Agilent 5973 Network Mass Selective Detector equipped with a 6890 gas chromatograph system and a HP-5MS capillary column (60 μm×0.25 mm×0.25 mm). Samples were analyzed in full scan mode using electron impact ionization; ion fragment peaks were integrated to calculate sterol abundance, and quantitation was relative to cholesterol-d7. The following ion fragments were used to quantitate each metabolite: cholesterol-d7 (465), cholesterol (368)(Sigma Aldrich), zymostenol (458), All standards were obtained from Avanti Polar Lipids unless otherwise indicated. Calibration curves were generated by injecting varying concentrations of sterol standards and maintaining a fixed amount of cholesterol-D7.

Figure 1B:
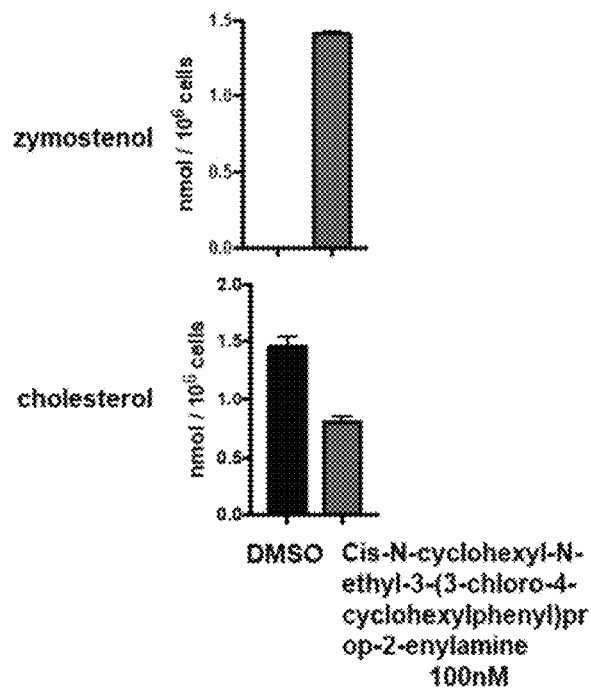
Figure 2:
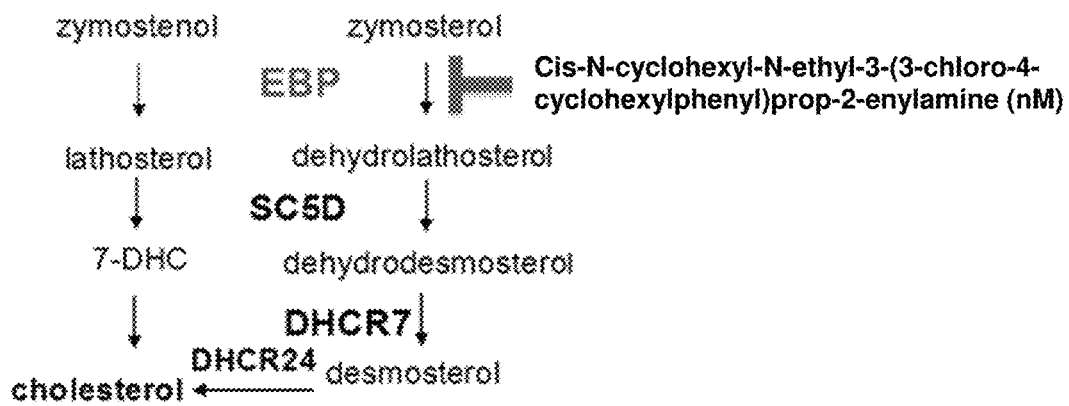
FIG. 2 is a schematic of the cholesterol biosynthesis pathway showing the point of inhibition by Cis-N-cyclohexyl-N-ethyl-3-(3-chloro-4-cyclohexylphenyl)prop-2-enylamine (referred to in FIG. 2 as the "Compound").

The results are shown in FIG. 1B. As can be seen from the figure, OPCs treated in culture with Cis-N-cyclohexyl-N-ethyl-3-(3-chloro-4-cyclohexylphenyl)prop-2-enylamine accumulate zymostenol and produce lesser amounts of cholesterol.

Figure 5:
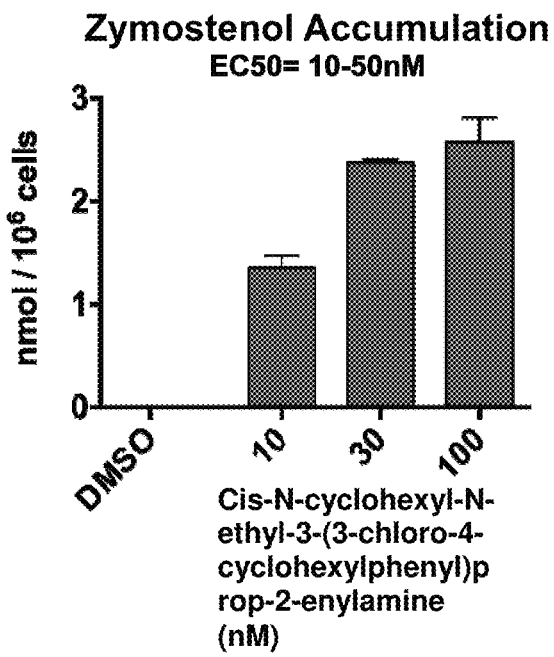
FIG. 5 is a bar graph illustrating the effect of Cis-N-cyclohexyl-N-ethyl-3-(3-chloro-4-cyclohexylphenyl)prop-2-enylamine (concentrations=10 nM, 30 nM, 100 nM) on EBP inhibition in mouse OPCs in vitro, which results in accumulation of EBP substrate zymostenol in OPCs.

The experiments described above were repeated with a wider range of concentrations for the compound Cis-N-cyclohexyl-N-ethyl-3-(3-chloro-4-cyclohexylphenyl)prop-2-enylamine (10 nM, 30 nM, 100 nM) and the results are shown in FIG. 5. FIG. 5 serves as corroborative evidence to FIG. 1B that OPCs treated in culture with Cis-N-cyclohexyl-N-ethyl-3-(3-chloro-4-cyclohexylphenyl)prop-2-enylamine accumulate zymostenol, which suggests that the presence of the compound Cis-N-cyclohexyl-N-ethyl-3-(3-chloro-4-cyclohexylphenyl)prop-2-enylamine in the mouse OPC cultures results in EBP inhibition.

Example 3—Cis-N-cyclohexyl-N-ethyl-3-(3-chloro-4-cyclohexylphenyl)prop-2-enylamine Causes Increased In Vivo Brain Level Zymostenol and Zymosterol and a Reduction of the Downstream Sterol Intermediate Desmosterol Cis-N-cyclohexyl-N-ethyl-3-(3-chloro-4-cyclohexylphenyl)prop-2-enylamine was dissolved in a vehicle solution containing 80/10/10 saline/DMSO/Kolliphor. C57-BL6 mice were injected at 10 mg/kg once daily for 3 days with either vehicle (DMSO) or Cis-N-cyclohexyl-N-ethyl-3-(3-chloro-4-cyclohexylphenyl)prop-2-enylamine (n=5). (5 mice/condition). After 3 days, mice were anesthetized with isoflurane and perfused with phosphate buffered saline to remove blood from the brain. Brains were collected and flash frozen using liquid nitrogen. The samples were pulverized and 50-100 milligrams of tissue were collected for further processing. A modified Folch protocol was used for extraction of sterols. Briefly, samples were resuspended in a 2:1 chloroform/methanol mixture and homogenized. Cell debris was removed by centrifugation at 4000 g for 10 min. The solution was dried under air and resuspended in hexane with a cholesterol-D7 standard and dried again. Lipids were derivatized with 70 ul of bis(trimethylsilyl) trifluoroacetamide; Samples were analyzed in ion monitoring mode using electron impact ionization; ion fragment abundances were integrated. 2 ul was analyzed by gas chromatography/mass spectrometry using an Agilent 5973 Network Mass Selective Detector equipped with a 6890 gas chromatograph system and a HP-5MS capillary column (60 μm×0.25 mm×0.25 mm). Samples were analyzed in full scan mode using electron impact ionization; ion fragment peaks were integrated to calculate sterol abundance, and quantitation was relative to cholesterol-d7. The following ion fragments were used to quantitate each metabolite: zymostenol (458), zymosterol (456), Desmosterol. All standards were obtained from Avanti Polar Lipids unless otherwise indicated. Calibration curves were generated by injecting varying concentrations of sterol standards and maintaining a fixed amount of cholesterol-D7.

Figure 3A:
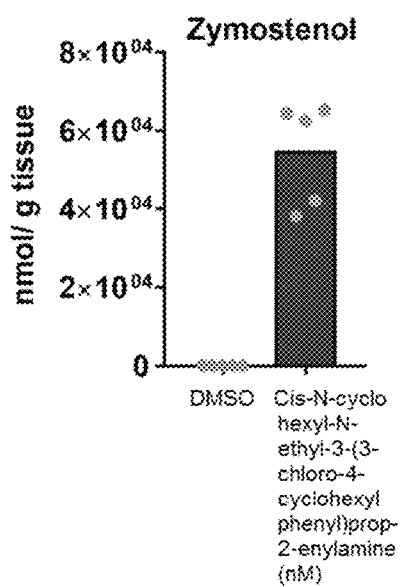
FIGS. 3(A-C) are bar graphs showing increased brain levels of zymostenol and zymosterol, the cholesterol intermediates upstream of EBP, concurrent with a reduction of downstream sterol intermediates (Desmosterol) following administration of Cis-N-cyclohexyl-N-ethyl-3-(3-chloro-4-cyclohexylphenyl)prop-2-enylamine to laboratory animals (referred to in FIGS. 3(A-C) as the "Compound").
Figure 3B:
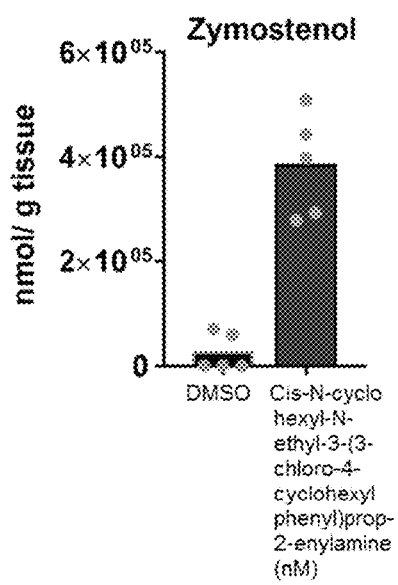
Figure 3C:
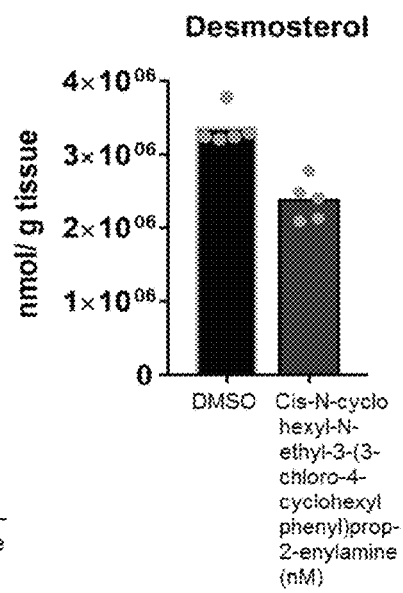

As can be seen from FIGS. 3A-3C, brain levels of zymostenol and zymosterol increased and brain levels of desmosterol decreased in mice treated with Cis-N-cyclohexyl-N-ethyl-3-(3-chloro-4-cyclohexylphenyl)prop-2-enylamine (referred to in FIGS. 3A-3C as the "Compound").

Example 4—Cis-N-cyclohexyl-N-ethyl-3-(3-chloro-4-cyclohexylphenyl)prop-2-enylamine Increases the Amount of Myelin Sheaths Formed on the Microfibers, In Vitro Oligodendrocyte formation and imaging on electrospun microfibers: A 12-well plate containing Mimetex aligned scaffold (microfiber plate, AMSBIO, AMS.TECL-006-1X, Electrospun poly-L-lactide Scaffold, 2 mM fibre diameter cell crown inserts) was prepared as previously described. Briefly, inserts were sterilized with 70% ethanol and washed with PBS before being coated with polyornithine and laminin. After laminin coating, 100,000 cells/mL of EpiSC-derived OPCs were plated in differentiation medium. After 24 h the media was replaced with fresh media containing small molecule treatments. Every 48 h the media was replaced with fresh compound containing media for a total of 12 days. Plates were fixed with 4% PFA, permeabilized with 0.1% Triton X-100, and blocked with 10% donkey serum (v/v) in PBS for 60 min. Plates were stained for MBP (Abcam, ab7349; 1:100) and DAPI staining (Sigma; 5 µg/ml). After staining, the inserts were moved into new 12-well plate and covered with 2 mL of PBS before imaging in Operetta high content Imaging and analysis system. Plates were imaged on the Operetta High Content Imaging and Analysis system (PerkinElmer) and a set of 8 fields captured from each well resulting in an average of 45,000 cells being scored per well. Analysis (PerkinElmer Harmony and Columbus software) identified intact nuclei stained by DAPI and calculated the MBP signal intensity per cell per well. Microfiber insert tracking images were taken using a Leica DMi8 with a 20x Dry/NA 0.40 objective. Microfiber plate inserts were mounted using Flouromount-G (SouthernBiotech) and allowed to partially harden before coverslips were added and the insert ring was removed.

The formation of myelin sheaths on the microfibers (which mimic the network of nerve fibers) when the OPCs were left untreated or treated with 100 nM of Cis-N-cyclohexyl-N-ethyl-3-(3-chloro-4-cyclohexylphenyl)prop-2-enylamine is compared using live microscopic images (not shown). These microscopic images indicate a significant increase in the amount of myelin sheaths formed on the electrospun poly-L-lactide scaffold microfibers with OPCs treated in vitro with the compound.

Example 5—Cis-N-cyclohexyl-N-ethyl-3-(3-chloro-4-cyclohexylphenyl)prop-2-enylamine Increases the Amount of Myelin Regulatory Factor-Positive (MYRF+) Human Oligodendrocytes in Human Cortical Spheroids, In Vitro Human cortical spheroids were generated as described in Madhavan et al, (Nature Methods, 15:700-706, 2018). In brief, spheroids were left untreated, or treated with Cis-N-cyclohexyl-N-ethyl-3-(3-chloro-4-cyclohexylphenyl)prop-2-enylamine (30 nM) from days 61-71 and assayed 2 at on day 94 for MyRF+ oligodendrocytes (Rabbit anti-MyRF antibody was generously provided by M. Wegner and used at 1:1000).

For patterning of neurocortical spheroids, pluripotent stem cell colonies cultured on vitronectin (Gibco; A14700) were lifted with dispase (Gibco; 17105-041) at 37° C. for 10 min. Intact colonies were transferred to individual low-adherence V-bottom 96-well plates (S-Bio Prime; MS-9096VZ) in 200 µl of spheroid starter media with 10 µM ROCK inhibitor Y-27632 (Calbiochem; 688001), 10 µM dorsopmorphin (Sigma; P5499), and 10 µM SB-431542 (Sigma; S4317). Spheroid starter media was DMEM/F12 (Invitrogen; 11320-033) containing 20% KnockOut Serum (Invitrogen; 12587-010), non-essential amino acids (Invitrogen; Ser. No. 11/140,050), Glutamax (Invitrogen; 35050061), β-mercaptoethanol, and 100 U/ml penicillin-streptomycin. The same media without ROCK inhibitor was used for the next 5 d, after which the media was changed to Neurobasal-A-based spheroid media. Neurobasal-A spheroid media was Neurobasal-A medium (Invitrogen; Ser. No. 10/888,022) with B-27 serum substitute without vitamin A (Invitrogen; 12587), Glutamax (Invitrogen; 35050061), and 100 U/ml penicillin-streptomycin. From day 7 to day 25, 20 ng/ml FGF-2 (R&D Systems; 233-FB-25/CF), and 10 ng/ml EGF (R&D Systems; 236-EG-200) were added to the media. Spheroids were cultured in 96-well plates through day 25, with daily half media changes. On day 25, spheroids were transferred to ultra-low-attachment six well plates (Corning; CLS3471) at a density of 8-10 spheroids per well and cultured thus through the remainder of the protocol. Also from this point forward, 1% Geltrex (Invitrogen; A15696-01) was added to the Neurobasal-A spheroid media. Neural differentiation was induced between days 27 and 41 by supplementation of Neurobasal-A spheroid media with 20 ng/ml BDNF (R&D Systems; 248-BD) and 20 ng/ml NT-3 (R&D Systems; 267-N). Half-media changes were performed every other day between days 17 and 41.

To generate oligocortical spheroids, beginning on day 50, the inventors added 10 ng/ml PDGF-AA (R&D Systems; 221-AA-050) and 10 ng/ml IGF-1 (R&D Systems; 291-G1-200) to the every-other-day media changes for 10 d. Next, on day 60, the inventors added 40 ng/ml 3,3',5-triiodothronine (T3; Sigma; ST2877) to the every-other-day media changes for 10 d. When used, small molecules were supplemented during this period. After day 70, spheroids were matured and maintained in Neurobasal-A spheroid media with every-other-day media changes until completion of the experiment.

Spheroids for immunohistochemistry were initially fixed with 4% ice-cold paraformaldehyde for 45 min, washed three times in PBS, and equilibrated with 30% sucrose overnight. The spheroids were embedded in OCT and sectioned at 10 µm. Immunohistochemistry was performed as described previously. Briefly, sections were washed in PBS three times and then blocked for 30 min in PBS containing 0.1% Triton X-100 and 0.25% normal donkey serum. The sections were then incubated at 4° C. overnight with primary antibodies in blocking solution. The inventors used the following primary antibodies: rabbit anti-MYRF (1:1,000; provided by Michael Wegner), and DAPI (1 µg/ml; Sigma; D8417). Sections were then washed in PBS and incubated in secondary antibodies for 2 h. All secondary antibodies were Life Technologies Alexa Fluor-conjugated secondary antibodies used at a dilution of 1:500. For counting of MYRF+ nuclei, four 20x fields were imaged per spheroid. Two fields from the top and bottom of the spheroid and two fields from the edges of the central region of the spheroids were quantified. The total numbers of DAPI-positive cells and MYRF+ oligodendrocytes were manually counted in Adobe Photoshop or NIH ImageJ. Three to five spheroids were analyzed per line and treatment condition, and GraphPad Prism was used to perform a t-test to assess statistically significant differences between lines or treatments.

The changes in the proliferation of DAPI-stained cells and MYRF+ oligodendrocytes in the untreated and treated human cortical spheroids were compared microscopic images of DAPI-stained cells (negative control) or MYRF+ cells of untreated human cortical spheroids and human cortical spheroids treated with 30 nM of Cis-N-cyclohexyl-N-ethyl-3-(3-chloro-4-cyclohexylphenyl)prop-2-enylamine in vitro (images not shown). Cis-N-cyclohexyl-N-ethyl-3-(3-chloro-4-cyclohexylphenyl)prop-2-enylamine was shown to have the ability to selectively increase MYRF+ oligodendrocytes in the human cortical spheroid model.

Figure 6:
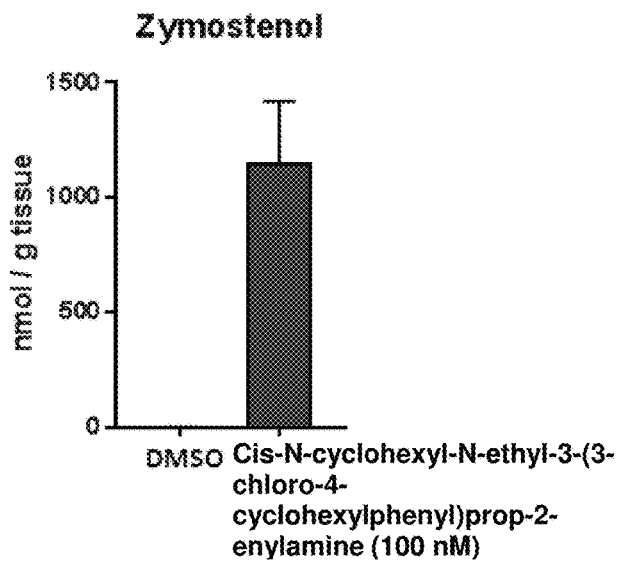
FIG. 6 is a bar graph illustrating the effect of Cis-N-cyclohexyl-N-ethyl-3-(3-chloro-4-cyclohexylphenyl)prop-2-enylamine (concentration=100 nM) on EBP inhibition in human cortical spheroid cells in vitro, which results in accumulation of EBP substrate zymostenol in the human cortical spheroid cells, thereby providing evidence of on-target human EBP inhibition.

Example 6—Cis-N-cyclohexyl-N-ethyl-3-(3-chloro-4-cyclohexylphenyl)prop-2-enylamine Causes Accumulation of EBP Substrate Zymostenol in Human Oligodendrocytes in Human Cortical Spheroids, Thereby Providing Evidence of In Vitro On-Target Inhibition of Human EBP Procedures undertaken to measure the level of zymstenol in human oligodendrocytes in human cortical spheroids treated with Cis-N-cyclohexyl-N-ethyl-3-(3-chloro-4-cyclohexylphenyl)prop-2-enylamine and the negative control of DMSO are as described in Example 2. The effect of Cis-N-cyclohexyl-N-ethyl-3-(3-chloro-4-cyclohexylphenyl)prop-2-enylamine (concentration=100 nM) on EBP inhibition in human cortical spheroid cells in vitro is illustrated in FIG. 6, which indicates accumulation of EBP substrate zymostenol in the human cortical spheroid cells, thereby providing evidence of on-target human EBP inhibition.

Figure 7A:
FIG. 7A illustrates the study programs.

Example 7—Treatment with Cis-N-cyclohexyl-N-ethyl-3-(3-chloro-4-cyclohexylphenyl)prop-2-enylamine Increases the In Vivo Generation of Newly Myelinated Fibers within the Spinal Cord Following Focal Demyelination, Thereby Providing Evidence of Enhanced In Vivo Remyelination Following Demyelination Focal demyelination in the dorsal column of the spinal cord was induced by the injection of 1% LPC solution. 12 week old C57BL/6 female mice were anesthetized using isoflurane and T10 laminectomies were performed. 4l of 1% LPC was infused into the dorsal column at a rate of 15 ul/hour. At day 4, as can be seen from FIG. 7A, animals were randomized into treatment groups prior to treatment. Between days 4 and 13 post laminectomy, animals received daily injections of either vehicle or drug intraperitoneally. Drugs were dissolved in 5% DMSO+5% Ethanol in saline for injections such that final doses were 25 mg/kg for Cis-N-cyclohexyl-N-ethyl-3-(3-chloro-4-cyclohexylphenyl)prop-2-enylamine. This experiment was done in a blinded manner: compounds were coded to ensure the researchers performing the experiments were unaware of the treatment being administered to each animal. All animals were euthanized 13 days post laminectomy (n=6 per group). Mice were anesthetized using ketamine/xylazine rodent cocktail and then euthanized by transcardial perfusion with 4% PFA, 2% glutaraldehyde, and 0.1 µM sodium cacodylate. Samples were osmicated, stained en bloc with uranyl acetate and embedded in EMbed 812, an Epon-812 substitute (EMS). 1 µm sections were cut and stained with toluidine blue and visualized on a light microscope (Leica DM5500B). The number of myelinated axons per unit area was counted from sections obtained from the middle of each lesion and then averaged over each treatment group. All sections within the lesion area were scored. A Mann-Whitney statistical analysis was performed to assess statistical significance.

Electron Microscopy: Samples were fixed for 1 h at room temperature in a fixative solution containing 4% paraformaldehyde (EMS), 2% glutaraldehyde (EMS), and 0.1 M Na-cacodylate (EMS). Samples were then osmicated, stained with uranyl acetate, and embedded in EMbed 812 (EMS). Ultrathin sections (120 nm) from each spheroid sample were observed with an FEI Helios NanoLab 660 FIBSEM field emission scanning electron microscope using extreme high resolution and equipped with a concentric (insertable) higher-energy electron detector. All images were taken using 4 kV and 0.2 current landing voltage at high magnification (15,000-35,000×).

Figures 7B, 7C:
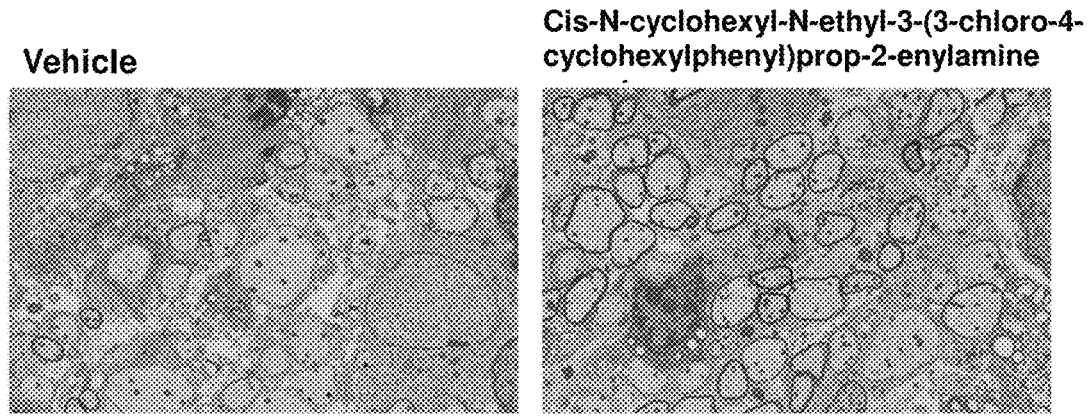
FIG. 7B and FIG. 7C are electron microscopic images of 1 µm cut section of the dorsal column of the spinal cord treated with vehicle solution (negative control) and treated with Cis-N-cyclohexyl-N-ethyl-3-(3-chloro-4-cyclohexylphenyl)prop-2-enylamine, respectively.

The dark rings surrounding the axons in FIG. 7C definitively show new myelin formation in the center of a previously demyelinated lesion, when the lesion is treated with Cis-N-cyclohexyl-N-ethyl-3-(3-chloro-4-cyclohexylphenyl)prop-2-enylamine. Comparatively, such dark rings are absent from FIG. 7B, when only the vehicle is present.

Figures 7D, 7E:
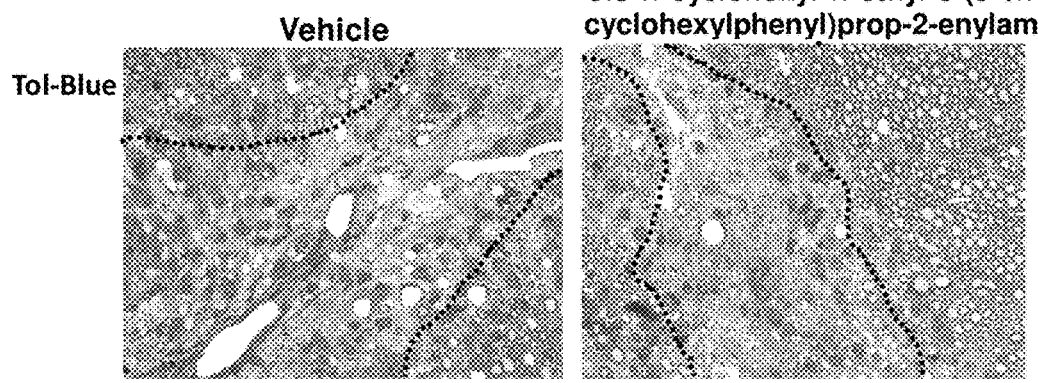
FIG. 7D and FIG. 7E are toluidine Blue-stained microscopic images of 1 µm cut section of the dorsal column of the spinal cord untreated (negative control) and treated with Cis-N-cyclohexyl-N-ethyl-3-(3-chloro-4-cyclohexylphenyl)prop-2-enylamine, respectively.
Figure 7F:
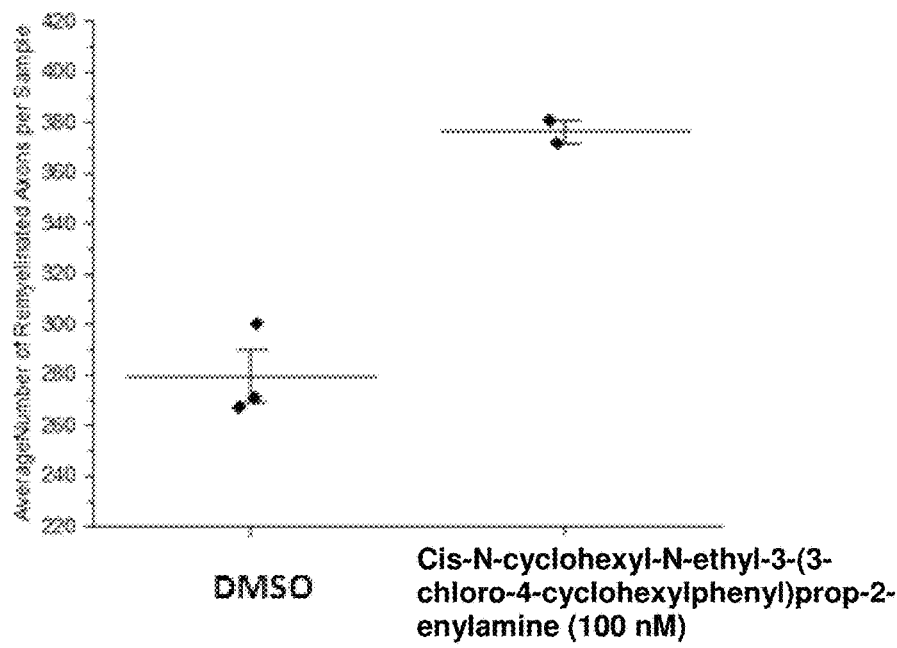
FIG. 7F shows that treatment with Cis-N-cyclohexyl-N-ethyl-3-(3-chloro-4-cyclohexylphenyl)prop-2-enylamine significantly increased the number of toluidine Blue-stained newly myelinated fibers within the spinal cord following focal demyelination, but not the negative control.

As with the toluidine Blue-stained images of FIG. 7D and FIG. 7E, the lesions are outlined by the dotted lines, with the lesion in the middle. The plurality of small circular structures surrounding the lesion in FIG. 7E indicates myelin formation, and since these structures are very small, they must be newly formed. Comparatively, these small circular structures are not present in FIG. 7D, where the lesion is left untreated. The quantification graph of remyelination of FIGS. 7D and 7E is presented in FIG. 7F. FIG. 7F clearly shows that the treatment with Cis-N-cyclohexyl-N-ethyl-3-(3-chloro-4-cyclohexylphenyl)prop-2-enylamine significantly increased the number of toluidine Blue-stained newly myelinated fibers within the spinal cord following focal demyelination, but not the vehicle.

Figure 8A:
FIG. 8A illustrates the study programs.

Example 8—Treatment with Cis-N-cyclohexyl-N-ethyl-3-(3-chloro-4-cyclohexylphenyl)prop-2-enylamine Leads to Noticeable In Vivo Recovery of Fractional Anisotropy (FA) Values Following Demyelination In total, 30 Sprague-Dawley male rats (~200-300 g) were infused with lysophosphatidylcholine (LPC) on the ipsilateral side and with vehicle for LPC on the contralateral side of the corpus callosum in order to induce demyelination. Three days thereafter, as can be seen in FIG. 8A, 15 animals per treatment group were randomly assigned to daily Test Compound or Vehicle intraperitoneal treatment groups and administration (20 mg/kg, 8.0 mL/kg, QD) was performed through 3-15 days after LPC infusion. Cis-N-cyclohexyl-N-ethyl-3-(3-chloro-4-cyclohexylphenyl)prop-2-enylamine was diluted to a final concentration of 2.5% ETOH and 2.5% Kolliphor in Saline. DTI-MRI was used as a primary method to quantify the demyelinated lesion and to assess the organization of white matter in corpus callosum over time, on days 3, 10 and 15. Day 3 served as a baseline followed by repeated analyses during the therapeutic period. On day 15, the animals were euthanized and tissue samples collected. The amount of demyelination and the extent of neuronal loss were analyzed by histological analysis of MBP and Nissl substance, respectively, in corpus callosum.

Demyelination in corpus callosum was induced by stereotactic infusion of lysophosphatidylcholine (LPC, Santa Cruz, Calif., USA) directly to the target tissue. First, rats were anesthetized with 5% isoflurane (in 70% N20 and 30% 02; flow 300 ml/min) and placed in a stereotactic frame. During the operation concentration of anesthetic was reduced to 1-1.5% for maintenance. Access to the left and right brain hemispheres was exposed through two small craniectomy holes in the skull.

Infusion of LPC to the corpus callosum was started by puncturing the dura mater with fine needle and a stereotaxic injection of 1% lysophosphatidylcholine (solution in PBS (pH 7.4) was made into the corpus callosum. The infusion needle was guided to desired coordinates and allowed to stabilize before the onset of infusions. A total of 1.5 µL of LPC solution was infused at a speed of 0.25 µL/min at the following coordinates (from bregma): AP −0.4, ML −/+1.4, DV −2.6 or −2.9 mm (from brain surface). Rats received LPC solution infusion to the left hemisphere. Contralateral (right hemisphere) side was similarly sham-infused with 1.5 µL vehicle for LPC. After the infusions, injection needle was left in place for another 5 min before being carefully withdrawn and the skin was closed and disinfected. The rats were then allowed to recover from anesthesia and were carefully monitored for possible post-surgical complications. After initial recovery, the animals were returned to the home cages with ad libitum access to food and water.

Analgesics were administered during and after the surgery. Fifteen minutes before infusion, rats received buprenorphine (Temgesic®, 0.03 mg/kg s.c.) and carprofen (Rimadyl®, 5.0 mg/kg, s.c.). Additional doses of buprenorphine 0.03 mg/kg were administered s.c. twice per day during the first 48 h. Additional doses of carprofen were administered once per day during the first 48 h. Rats were carefully monitored by laboratory personnel twice a day and any rats prematurely fulfilling the criteria for humane endpoints were euthanized during the study.

MRI acquisitions were performed at day 3, 10 and 15 post LPC infusion using a horizontal 11.7.T magnet with a bore size of 160 mm, equipped with a gradient set capable of max. gradient strength of 750 mT/m and interfaced to a Bruker Avance III console (Bruker Biospin GmbH, Ettlingen, Germany). A volume coil (Bruker Biospin GmbH, Ettlingen, Germany) was used for transmission and a surface phased array coil for receiving (Rapid Biomedical GmbH, Rimpar, Germany). Rats were anesthetized using isoflurane, fixed to a head holder and positioned in the magnet bore in a standard orientation relative to gradient coils. After acquisition of fast localizer images, diffusion tensor MRI (DTI) was performed using segmented EPI sequence with 30 diffusion directions (b-values 0 and 970 s/mm$^2$). Field-of-view of 20×13.3 mm2 was used with matrix of 256×160 resulting 100 microns in-plane resolution. Seven 0.7 mm slices were acquired with 4 averages; middle slice was placed to the level of infusion tract visible in the axial localizer MR images. Diffusion tensor was estimated under FSL software and fractional anisotropy values were evaluated from FA images for lesion on the ipsilateral side and same region for each animal is analyzed from contralateral corpus callosum.

Figure 8B:
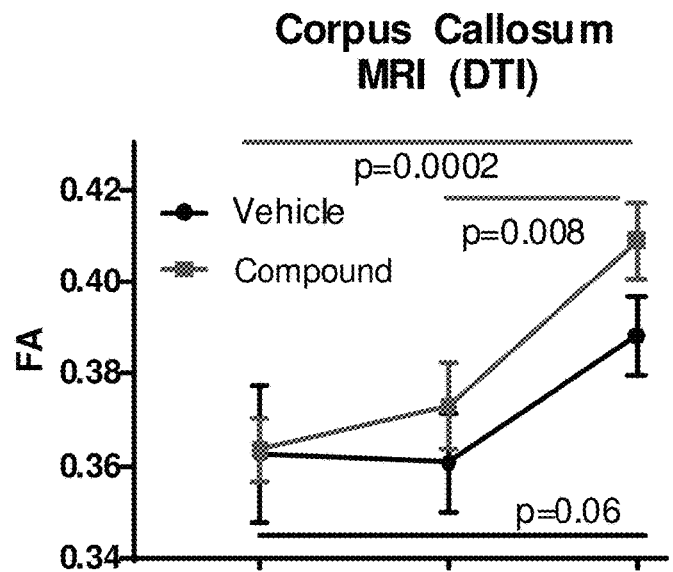
FIG. 8B is a graph showing the FA values of the ipsilateral sideuntreated and treated with 5 mL/kg of Cis-N-cyclohexyl-N-ethyl-3-(3-chloro-4-cyclohexylphenyl)prop-2-enylamine. Treatment with Cis-N-cyclohexyl-N-ethyl-3-(3-chloro-4-cyclohexylphenyl)prop-2-enylamine resulted in noticeable recovery of the FA value.

FIG. 8B is a graph showing the FA values of the ipsilateral side untreated and treated with 5 mL/kg of Cis-N-cyclohexyl-N-ethyl-3-(3-chloro-4-cyclohexylphenyl)prop-2-enylamine. Treatment with Cis-N-cyclohexyl-N-ethyl-3-(3-chloro-4-cyclohexylphenyl)prop-2-enylamine resulted in noticeable recovery of the FA value. Furthermore, FIG. 8B shows a trend in improvement between the groups at Day 15 by ipsilateral FA measurements.

All publications and patents mentioned in the above specification are herein incorporated by reference.

What is claimed is:

1. A method of treating a subject with primary progressive multiple sclerosis, comprising administering an effective amount of Cis-N-cyclohexyl-N-ethyl-3-(3-chloro-4-cyclohexylphenyl)prop-2-enylamine or a pharmaceutically acceptable salt thereof to the subject.

2. A method of treating a subject with secondary progressive multiple sclerosis, comprising administering an effective amount of Cis-N-cyclohexyl-N-ethyl-3-(3-chloro-4-cyclohexylphenyl)prop-2-enylamine or a pharmaceutically acceptable salt thereof to the subject.

* * * * *